(12) United States Patent
De Simone

(10) Patent No.: US 7,323,317 B2
(45) Date of Patent: *Jan. 29, 2008

(54) ANALYTICAL METHOD FOR DETECTING ALKALINE SPHINGOMYELINASE AND KIT FOR USE IN SUCH METHOD

(75) Inventor: Claudio De Simone, Ardea RM (IT)

(73) Assignee: VSL Pharmaceuticals, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/712,417

(22) Filed: Mar. 1, 2007

(65) Prior Publication Data

US 2007/0154974 A1  Jul. 5, 2007

Related U.S. Application Data

(60) Continuation of application No. 11/359,619, filed on Feb. 23, 2006, now Pat. No. 7,211,410, which is a division of application No. 10/499,336, filed as application No. PCT/IT02/00811 on Dec. 19, 2002, now abandoned.

(30) Foreign Application Priority Data

Dec. 21, 2001 (IE) .................................. 2001/1100

(51) Int. Cl.
*C12Q 1/44* (2006.01)
(52) U.S. Cl. ........................................................ 435/19
(58) Field of Classification Search ...................... None
See application file for complete search history.

(56) References Cited

U.S. PATENT DOCUMENTS 6,265,179 B1  7/2001  Zhou et al.

FOREIGN PATENT DOCUMENTS

WO  WO 03/056031 A2  7/2003

OTHER PUBLICATIONS

Biocompare website "Amplex Red Sphingomyelinase Assay Kit" first available on web 1999, 3 pages (2005).
Finneran e-mail on "Amplex Red Sphingomyelinase Assay Kit" released May 12, 1999, 1 page (2005).
"Amplex Red Sphingomyelinase Assay Kit (A12220)" Molecular Probes Product Information, Revised, 4 pages (Jan. 2001).
"Amplex Red Sphingomyelinase Assay Kit (A12220)" Invitrogen/Molecular Probes Product Information, Revised, 4 pages (Oct. 2004).
Denisova et al. "Role of membrane lipids in regulation of vulnerability to oxidative stress in PC12 cells: Implication for aging." Free Radical Biol. Med. 30:671-678 (2001).
Duan et al. "Effects of Ursodeoxycholate and other bile salts on levels of rat intestinal alkaline sphingomyelinase: A potential implication in tumorigenesis" Dig Dis & Sci. 43:26-32 (1998).
Goni et al. "Sphingomyelinases: Enzymology and membrane activity" FEBS Letter 531:38-46 (2002).
He et al. "A fluorescence-based, high-throughput sphingomyelin assay for the analysis of Niemann-Pick disease and other disorders of sphingomyelin metabolism." Anal. Biochem. 306:115-123 (2002) Abstract.
Hertervig et al. "Alkaline sphingomyelinase activity is decreased in human colorectal carcinoma" Cancer 79:448-453 (1997).
Sofic et al. "Antioxidant and pro-oxidant capacity of catecholamines and related compounds. Effects of hydrogen peroxide on glutathione and spingomyelinase activity in pheochromocytoma PC12 cells: Potential relevance to age-related diseases." J. Neural Trans. 108:541-557 (2001).
Zhang et al. "Involvement of the acid sphingomyelinase pathway in UVA-induce apoptosis" J. Biol. Chem. 276:11775-11782 (2001).
Int'l Search Report for Int'l Appln. No. PCT/IT02/00811 dated Oct. 10, 2003.

*Primary Examiner*—Michael Wityshyn
*Assistant Examiner*—Amanda P. Wood
(74) *Attorney, Agent, or Firm*—Nixon & Vanderhye P.C.

(57) ABSTRACT

An analytical fluorometric method and a kit for use in such method are disclosed for assessing the presence of alkaline sphingomyelinase (SMase) in the stool of a patient in need of such an assessment since alkaline SMase is a marker of serious pathological states, such as colon cancer.

18 Claims, 1 Drawing Sheet

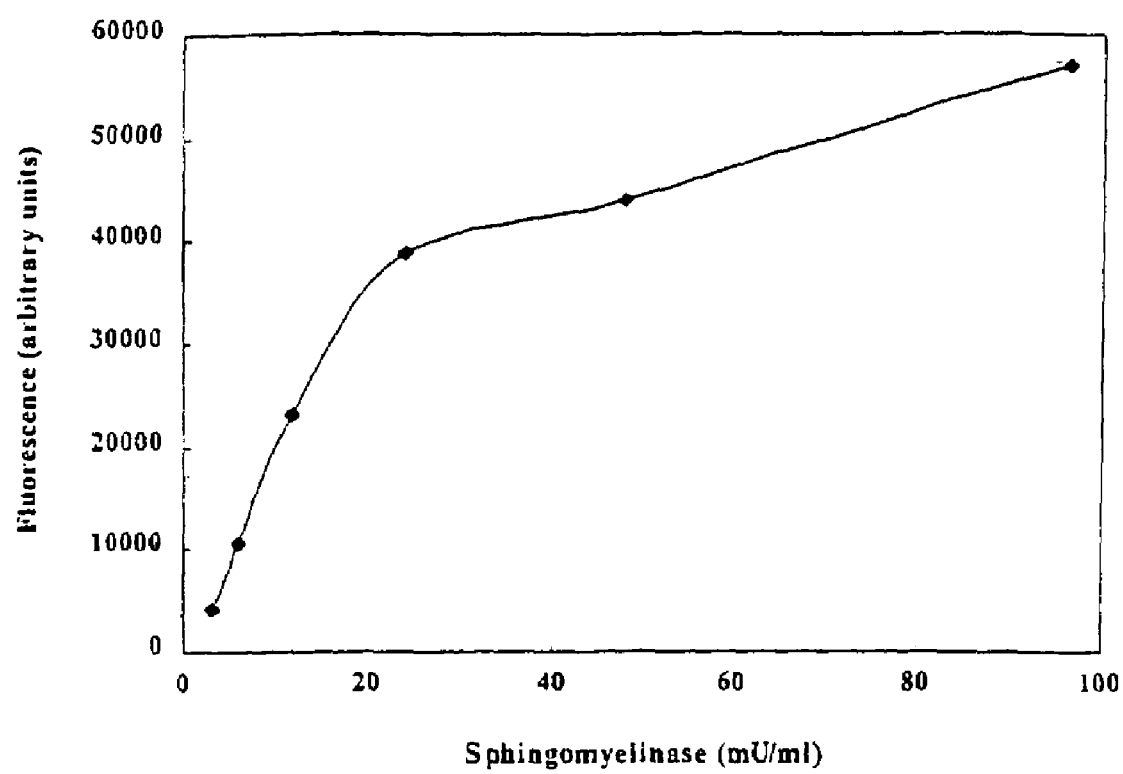

ANALYTICAL METHOD FOR DETECTING ALKALINE SPHINGOMYELINASE AND KIT FOR USE IN SUCH METHOD

CROSS-REFERENCE TO RELATED APPLICATIONS

This application is a continuation of application Ser. No. 11/359,619, filed Feb. 23, 2006, now U.S. Pat. Ser. 7,211,410; which is a division of application Ser. No. 10/499,336, filed Jun. 17, 2004, now abandoned; which is a U.S. national phase of Application No. PCT/IT02/00811, filed Dec. 19, 2002; the contents of which are incorporated herein by reference.

BACKGROUND OF THE INVENTION

The present invention relates to an analytical method for assessing the presence of alkaline sphingomyelinase in the stools or biological fluids of patients in need of such an assessment. The invention also relates to a kit for carrying out the analytical method.

More particularly the method of the present invention is an in vitro fluorometric method for detecting alkaline sphingomyelinase which, as will be described in detail hereinbelow, is a marker of serious pathological states such as colon cancer and familial adenomatous polyposis.

The enzyme sphingomyelinase (sphingomyelin phosphodiesterase, SMase) catalyzes the hydrolysis of sphingomyelin to ceramide and choline phosphate.

Three different types of SMase (acidic, neutral and alkaline) have been identified to-date, which occur as several isoforms, as follows:

lysosomal acidic SMase (A-SMase);
cytosolic $Zn^{2+}$-dependent acidic SMase;
membrane neutral magnesium-dependent SMase (N—SMase);
cytosolic magnesium-independent N—SMase; and
alkaline SMase.

SMases have been shown to play a role in a wide variety of physiologic and pathological processes, including: lysosomal hydrolysis of endocytosed SM, ceramide mediated cell signaling, atherogenesis, terminal differentiation, cell cycles arrest, apoptosis, inflammation, and the regulation of eukaryotic stress responses.

In contrast to acidic and neutral SMase, which are currently present in cells as lysosomal and membrane-bound enzymes, respectively, alkaline SMase exhibits tissue and species difference. In human beings, the alkaline SMase is found in intestinal mucosa and bile. Alkaline SMase starts to appear in the duodenum, reaches a high level in the intestine, especially in the distal part of the jejunum, and occurs in considerable amounts in the colon and rectum. This SMase presents optimal alkaline pH at 9.0, is $Mg^{2+}$-independent, bile salt-dependent and trypsin-resistant.

The pathological importance of alkaline SMase has only recently been recognized and this has prompted several studies to be carried out, mainly for the following reasons.

First, the enzyme may be responsible for the hydrolysis of the dietary sphingomyelin occurring substantially in milk, eggs, meat and fish. Second, this enzyme may regulate cholesterol absorption. Third, the presence of alkaline SMase along the intestinal tract and its selective decrease detected in colorectal carcinoma suggests that this enzyme plays a role in intestinal carcinogenesis, since under physiological conditions, it stimulates apoptosis and protects the intestinal mucosa against carcinogenesis.

Previous studies have also shown that, under physiological conditions, alkaline SMase is dissociated by bile salts from intestinal mucosal membrane to the lumen. However, under pathological conditions, whereby bile salt concentration is abnormally increased, the dissociation of alkaline SMase by bile salts may exceed the biosynthesis of the enzyme, resulting in a low level of activity of alkaline SMase in the mucosa, and an abnormally increased excretion of the enzyme in the feces or in biological fluids, i.e., bile. Consequently, the excess of alkaline SMase excreted in the stools or in biological fluids over normal, basal values, may be interpreted as a valuable diagnostic marker for colon rectal carcinoma and familial adenomatous polyposis, hence; the need of a reliable assay for detecting alkaline SMase in the stools or in biological fluids of patients likely to be suffering from the aforesaid pathologies of the intestinal tract.

In addition, some bacteria strains (e.g., *Streptococcus htermophilus* or *Lactobacilli*) contain high levels of SMase, and the assessment of alkaline SMase may provide a method to evaluate changes in the number of said bacteria, i.e., after a treatment with probiotics or/and probiotic-based products.

Previous methods for assaying alkaline SMase are already known. The activity of the SMases can be determined either in vivo through cell labeled with a radioactive precursor of SM and then determining the labeling product levels or in vitro using radiolabeled SM or a chromogenic analog of SM or colored and fluorescent derivatives of neutral SM.

These known commonly used assays are not entirely satisfactory since they are potentially very hazardous insofar as they are radioactive assays and less sensitive than a fluorometric assay.

SUMMARY OF THE INVENTION

An object of the present invention is to provide a reliable, unexpensive assay for alkaline SMase in the stools or biological fluids of patients likely to suffer from colorectal carcinoma and familial adenomatous polyposis, or gall bladder or liver diseases, which overcomes the drawbacks of the known methods.

A further object of the present invention is to provide an analytical kit for use in the aforesaid assay.

Another object of the present invention is the assessment of bacterial colonization in different health conditions or following diseases or treatment with drugs or probiotics or food supplements.

The fluorometric, indirect assay method of the present invention is grounded on the following sequence of reactions.

Under the action of alkaline SMase, present in feces or other biological materials, sphingomyelin is hydrolyzed to ceramide and phosphorylcholine which, under the action of alkaline phosphatase, is hydrolyzed yielding choline. In the presence of choline oxidase, choline produces hydrogen peroxide ($H_2O_2$).

This latter compound, in the presence of horse-radish peroxidase, is caused to react with 10-acetyl-3,7-dihidroxyphenoxazine, a sensitive fluorogenic probe for $H_2O_2$ (hereinbelow referred to as "Amplex Red Reagent") yielding the highly fluorescent compound resorufin. Fluorescence is measured with a fluorocount microplate fluorometer using excitation at 530-560 nm and fluorescence detection at 590 nm.

BRIEF DESCRIPTION OF THE DRAWING

FIG. 1 shows detection of sphingomyelinase using the fluorescence assay. Each reaction contained the indicated amount of bacterial sphingomyelinase in specific assay buffer. Reactions were incubated at 37° C. for one hour. Fluorescence was measured with a fluorescence microplate reader using excitation at 530 nm and fluorescence detection at 590 nm.

DESCRIPTION OF SPECIFIC EMBODIMENTS OF THE INVENTION

Based on the aforesaid reaction sequence and fluorescence detection means, the assay method of the present invention for assaying alkaline SMase comprises the following steps which refers to stools. However, it will be apparent to a person skilled in the art that this method can be easily applied also to biological fluids such as bile with appropriate routine variations, 1) collecting a sample of a patient's stools and drying it up;

2) weighing about 3-4 grams of the dried up sample and suspending it in 20 ml of a homogenization buffer containing 0.25 M sucrose, 0.15 M KCl, 50 mM $KH_2PO_4$, pH 7.4;

3) centrifuging the sample at 4000 rpm at +4° C. for 60 min;

4) recovering the supernatant and centrifuging again for 15 min. at 4000 rpm at +4° C.;

5) measuring protein content in supernatant with the Pierce Protein Assay with bovine serum albumin as standard using for each sample a range of protein concentration between 32 mg/ml and 40 mg/ml and pipetting 25 µl of each sample into well;

6) adding to each 25 µl sample 65 µl of assay buffer containing 50 mM Tris/HCl, 2 mM EDTA, 0.15 M NaCl pH 9.0 and 10 µl of 29 µM sphingomyelin and in assay buffer adding bile salts (TC, TDC, GC, GCDC) in the concentration of 3 mM;

7) incubating at 37° C. for 1 hr;

8) pipetting 100 µl of each standard (see below) and 10 µl of sphingomyelin (29 µM), incubating for 1 hr at 37° C. as the samples;

9) after 1 hour, adding 100 µl of reaction buffer containing 50 mM Tris/HCl pH 7.4, 10 mM β-glycerophosphate, 750 µM ATP, 5 mM EDTA, 5 mM EGTA, 100 µM Amplex Red, 8 U/ml alkaline phosphatase, 0.2 U/ml choline oxidase, 2 U/ml horseradish peroxidase;

10) incubating the reactions for 1 hour or longer at 37° C., protected from light;

11) measuring the fluorescence in a fluorescence microplate reader using excitation in the range of 530-560 nm and emission detection at 590 nm;

12) for each point, correcting for background fluorescence by subtracting the values derived from the no-sphingomyelinase control.

The invention also relates to a kit for detecting alkaline sphingomyelinase in a patient's stools or biological fluids according to the previously disclosed method, which comprises test tubes separately containing samples of the following reagents:

a) sphingomyelin to be hydrolized by alkaline sphingomyelinase present in the stools or biological fluids, to give phosphorylcholine;

b) alkaline phosphatase for catalyzing the hydrolysis of phosphorylcholine to choline;

c) choline oxidase for oxidizing choline to hydrogen peroxide;

d) horse-radish peroxidase for assisting reaction of hydrogen peroxide with e) AmpleX Red Reagent (10-acetyl-3,7-dihydroxyphenoxazine) to give the fluorescent compound resorufin whose fluorescence is a marker of the alkaline SMase present in the stools or biological fluids; and f) lyophilized bacterial sphingomyelinase for use as standard concentrate.

For the analytical method of the present invention to be suitably carried out, in addition to the aforesaid kit components, the following further materials and equipments are required:

Sucrose;
Potassium chloride (KCl);
Potassium phosphate, monobasic ($KH_2PO_4$);
Trizma base;
EDTA;
Sodium chloride;
Taurocholate (TC);
Taurodeoxycholate (TDC);
Glycocholate (GC);
Glycochenodeoxycholate (GCDC);
β-glycerophosphate;
ATP disodium salt;
EGTA;
BCA Protein Assay Reagent;
Bovine serum albumin;
A refrigerated centrifuge;
A microplate reader capable of measurement at 550-562 nm, and
A fluorocount microplate fluorometer.

In order to accomplish the quantification of SMase activity, the following measures should be taken.

Standard Curve Preparation

The kit is supplied with a standard preparation of SMase, it consists of bacterial extract containing a type of SMase that works at pH 9. The following operations should be performed.

Generate a SMase calibration curve: dilute the standard concentrate to make serial dilutions.

Reconstitute the SMase standard with 1 ml of assay buffer (pH 9.0); this reconstitution produces a stock solution of 96 mU/ml.

Pipette 0.500 ml of assay buffer into each tube. Use the stock solution to produce a dilution series. Mix each tube thoroughly before the next transfer. The undiluted standard serves as the high standard (96 mU/ml), and the standard curve will contain the following concentrations (mU/ml): 96-48-24-12-6-3. Buffer serves as the zero standard (0 mU/ml).

Typical Standard Curves

In FIG. 1 the standard curve is shown for demonstration only. A standard curve should be generated for each set of samples assayed.

Calculation of Results

Average the duplicate readings for each standard and sample and subtract the average zero standard fluorescence.

Plot the fluorescence for the standards versus the activity (mU/ml) of the standards and draw the best curve. To determine the SMase activity of each sample, first find the fluorescence value on the y-axis and extend a horizontal line to the standard curve. At the point of intersection, extend a vertical line to the x-axis and read the corresponding SMase activity.

The described method is able to assay SMase activity in vitro; it has been developed with the intent to detect alkaline SMase in an organic sample.

To assay specifically the alkaline SMase the method uses conditions that detect the acid and neutral SMases activity. In fact:

the homogenization buffer is at neutral pH, but it does not have protease and phosphatase inhibitors to exclude the neutral SMase since the latter is sensitive to activities of proteases and phosphatases and is consequently inhibited by these enzymes;

in the homogenization buffer, $MgCl_2$ is absent to block the activity of $Mg^{2+}$ dependent neutral SMase; and the reaction buffer contains β-glycerophosphate and ATP to preclude acid SMase moreover activity at neutral pH, in this buffer EDTA and EGTA are present in high concentration to inhibit neutral SMase.

What is claimed is:

1. A kit for qualitatively or quantitatively detecting alkaline sphingomyelinase, said kit comprising the following components in separate containers:
(a) an assay buffer at pH 8.9-9.1 which contains EDTA in an amount sufficient to inhibit neutral sphingomyelinase;
(b) sphingomyelin;
(c) bile salts;
(d) a reaction buffer which contains EDTA and EGTA in amounts sufficient to inhibit neutral sphingomyelinase, and β-glycerophosphate and ATP in amounts sufficient to inhibit acid sphingomyelinase; (e) alkaline phosphatase; (f) choline oxidase;
(g) horseradish peroxidase; and
(h) fluorogenic probe for $H_2O_2$.

2. The kit of claim 1 further comprising bacterial alkaline sphingomyelinase, which is active at pH 9, of a known amount to be used for generating an alkaline sphingomyelinase standard curve.

3. The kit of claim 1, wherein the fluorogenic probe is 10-acetyl-3,7-dihydroxyphenoxazinedihydroxyphenotiazine.

4. A method for determining the concentration of alkaline sphingomyelinase in a biological sample, said method comprising:
(a) collecting, drying, and suspending the sample in a homogenization buffer;
(b) centrifuging the suspended sample to obtain a supernatant;
(c) adding to at least a portion of the supernatant (i) an assay buffer at pH 8.9-9.1 which contains EDTA in an amount sufficient to inhibit neutral sphingomyelinase, (ii) sphingomyelin, and (iii) bile salts and incubating for at least 1 hour;
(d) adding (i) a reaction buffer which contains EDTA and EGTA in amounts sufficient to inhibit neutral sphingomyelinase, and β-glycerophosphate and ATP in amounts sufficient to inhibit acid sphingomyelinase, (ii) alkaline phosphatase, (iii) choline oxidase, (iv) horseradish peroxidase, and (v) fluorogenic probe for $H_2O_2$ to one or more of the portions of supernatant and assay buffer obtained in (c) and incubating for 1 hour or longer at 37° C.;
(e) measuring fluorescence of the one or more of the portions of supernatant, assay buffer, and reaction buffer obtained in (d) with correction for background fluorescence by subtracting a negative control's fluorescence to obtain fluorescence value(s);
(f) performing a method comprising (a) to (e) using known concentrations of bacterial sphingomyelinase, which is active at pH 9, instead of the sample to obtain fluorescence values for an alkaline sphingomyelinase standard curve; and
(g) comparing the fluorescence values obtained in (e) and (f) to determine the concentration of alkaline sphingomyelinase in the sample.

5. The method according to claim 4, wherein the fluorogenic probe for $H_2O_2$ is 10-acetyl-3,7-dihydroxyphenoxazine.

6. The method according to claim 4, wherein the sample comprises a biological fluid.

7. The method according to claim 6, wherein the biological fluid is bile.

8. The method according to claim 4, wherein the sample comprises a biological material.

9. The method according to claim 8, wherein the biological material is human feces.

10. The method according to claim 4, wherein the sample comprises bacteria which produce alkaline sphingomyelinase.

11. A method for detecting alkaline sphingomyelinase in a biological sample, said method comprising:
(a) collecting, drying, and suspending the sample in a homogenization buffer;
(b) centrifuging the suspended sample to obtain a supernatant;
(c) adding to at least a portion of the supernatant (i) an assay buffer at pH 8.9-9.1 which contains EDTA in an amount sufficient to inhibit neutral sphingomyelinase, (ii) sphingomyelin, and (iii) bile salts and incubating for at least 1 hour;
(d) adding (i) a reaction buffer which contains EDTA and EGTA in amounts sufficient to inhibit neutral sphingomyelinase, and β-glycerophosphate and ATP in amounts sufficient to inhibit acid sphingomyelinase, (ii) alkaline phosphatase, (iii) choline oxidase, (iv) horseradish peroxidase, and (v) fluorogenic probe for $H_2O_2$ to one or more of the portions of supernatant and assay buffer obtained in (c) and incubating for 1 hour or longer at 37° C.;
(e) measuring fluorescence of the one or more of the portions of supernatant, assay buffer, and reaction buffer obtained in (d) with correction for background fluorescence by subtracting a negative control's fluorescence to obtain fluorescence value(s); and
(f) determining whether the sample contains alkaline sphingomyelinase from the fluorescence value(s).

12. The method according to claim 11, wherein the fluorogenic probe for $H_2O_2$ is 10-acetyl-3,7-dihydroxyphenoxazine.

13. The method according to claim 11, wherein the sample comprises a biological fluid.

14. The method according to claim 13, wherein the biological fluid is bile.

15. The method according to claim 11, wherein the sample comprises a biological material.

16. The method according to claim 15, wherein the biological material is human feces.

17. The method according to claim 11, wherein the sample comprises bacteria which produce alkaline sphingomyelinase.

18. A kit for qualitatively or quantitatively detecting alkaline sphingomyelinase, said kit comprising the following first and second components:
(a) a first component comprising
  (i) an assay buffer at pH 8.9-9.1 which contains EDTA in an amount sufficient to inhibit neutral sphingomyelinase;
  (ii) sphingomyelin; and
  (iii) bile salts; and
(b) a second component comprising
  (i) a reaction buffer which contains EDTA and EGTA in amounts sufficient to inhibit neutral sphingomyelinase, and β-glycerophosphate and ATP in amounts sufficient to inhibit acid sphingomyelinase;
  (ii) alkaline phosphatase;
  (iii) choline oxidase;
  (iv) horseradish peroxidase; and
  (v) fluorogenic probe for $H_2O_2$.

* * * * *